United States Patent
Berg et al.

(10) Patent No.: US 10,925,540 B2
(45) Date of Patent: Feb. 23, 2021

(54) GARMENT WITH CONDUCTIVE THREAD EXPOSED ON BOTH SIDES

(71) Applicant: Mad Apparel, Inc., Redwood City, CA (US)

(72) Inventors: James Artel Berg, Redwood City, CA (US); Hamid Hameed Butt, Cupertino, CA (US); Liang Yao, Toronto (CA); Gaston J. MacMillan, Oakland, CA (US); J. M. Hasitha B. Jayasundara, Panadura (LK)

(73) Assignee: Mad Apparel, Inc., Redwood City, CA (US)

( * ) Notice: Subject to any disclaimer, the term of this patent is extended or adjusted under 35 U.S.C. 154(b) by 1008 days.

(21) Appl. No.: 15/239,838

(22) Filed: Aug. 18, 2016

(65) Prior Publication Data
US 2018/0049698 A1    Feb. 22, 2018

(51) Int. Cl.
| | |
|---|---|
| A61B 5/04 | (2006.01) |
| A61B 5/00 | (2006.01) |
| A61B 5/0408 | (2006.01) |
| A61B 5/0492 | (2006.01) |
| A41D 1/00 | (2018.01) |

(52) U.S. Cl.
CPC ............ *A61B 5/6804* (2013.01); *A41D 1/005* (2013.01); *A61B 5/0408* (2013.01); *A61B 5/0492* (2013.01); *A61B 2562/0209* (2013.01); *A61B 2562/125* (2013.01)

(58) Field of Classification Search
CPC . A61B 5/04085; A61B 5/0006; A61B 5/6804; A61B 5/0408; A61B 5/0024; A61B 5/0402; A61B 5/6833; A61B 2560/0412; A61B 5/04012; A61B 5/04087; A61B 5/04028; A61N 1/0484; A61N 1/0456; A61N 1/0492; A61N 1/3925
USPC ........................ 600/372, 382–393, 508–509; 607/115–118
See application file for complete search history.

(56) References Cited

U.S. PATENT DOCUMENTS

| | | | | |
|---|---|---|---|---|
| 5,450,845 | A * | 9/1995 | Axelgaard | A61B 5/0408 600/382 |
| 9,775,561 | B2 * | 10/2017 | Russell | A61B 5/0024 |
| 10,398,335 | B2 * | 9/2019 | Kronstedt | A61B 5/04085 |
| 2007/0285868 | A1 * | 12/2007 | Lindberg | A61B 5/0245 600/382 |

(Continued)

*Primary Examiner* — Joseph A Stoklosa
*Assistant Examiner* — Brian M Antiskay
(74) *Attorney, Agent, or Firm* — Fenwick & West LLP

(57) ABSTRACT

A garment can be manufactured by bonding an adhesive to a first layer of fabric and a second layer of fabric. Holes are cut into each layer of fabric to accommodate the integration of sensors and a processing unit mount. Conductive thread embroidered onto a support layer is bonded to the adhesive of the second layer of fabric. The support layer is removed such that the conductive thread remains bonded to the adhesive. The layers of fabric are bonded together such that the conductive thread is coupled between the two layers of adhesive. A back plate is added to the layers of fabric to provide structural support for the mount. The conductive thread is exposed within each hole, and the mount and sensors can be coupled within the holes such that an electrical connection is established between the mount and at least one sensor via the conductive thread.

19 Claims, 8 Drawing Sheets

(56) References Cited

U.S. PATENT DOCUMENTS

| | | | | |
|---|---|---|---|---|
| 2008/0287770 A1* | 11/2008 | Kurzweil | ............ | A61B 5/0408 600/388 |
| 2009/0270708 A1* | 10/2009 | Shen | ................ | A61B 5/02438 600/389 |
| 2010/0081913 A1* | 4/2010 | Cross | .................. | A61B 5/6833 600/386 |
| 2015/0087951 A1* | 3/2015 | Felix | ................ | A61B 5/04085 600/382 |
| 2015/0094558 A1* | 4/2015 | Russell | ............... | A61B 5/6833 600/391 |
| 2016/0270727 A1* | 9/2016 | Berg | .................... | A61B 5/0006 |
| 2016/0374615 A1* | 12/2016 | Tsukada | ............ | A61B 5/04085 600/382 |
| 2017/0036066 A1 | 2/2017 | Chahine | | |
| 2017/0319132 A1* | 11/2017 | Longinotti-Buitoni | ..................... | A61B 5/0002 |

\* cited by examiner

GARMENT WITH CONDUCTIVE THREAD EXPOSED ON BOTH SIDES

BACKGROUND

1. Field of Art

This description generally relates to layered garments, and specifically to manufacturing layered garments with exposed conductive material on both sides of the garments.

2. Description of the Related Art

Sensors record a variety of information about the human body. For example, electrocardiograph (ECG) electrodes can measure electrical signals from the skin of a person that are used to determine the person's heart rate. In addition, electromyography (EMG) electrodes can measure electrical activity generated by a person's muscles. Heart rate and muscle movement information may be useful for evaluating the person's physiological condition, for instance, while exercising. The electrodes need to be positioned on, and physically contact, the person's skin. Often, ECG, EMG, and other types of electrodes are used in laboratories or other controlled settings where there is specialized equipment and personnel to help attach the electrodes to a person's skin.

Conductive threads have been used in garments to incorporate electronics components such as electrodes and other types of sensors. In particular, electrical signals from the sensors can be transmitted through conductive threads. Existing methods for manufacturing garments with conductive threads are time consuming because the methods require many steps to reliably embed the conductive threads into fabric of garments. Further, individually insulating each conductive thread in a garment increases the diameter of the conductive threads, which may be undesirable because the garment's thickness would increase as well.

SUMMARY

A garment includes multiple layers of material, including fabric, adhesives, and conductive threads. Further, the garment may also include sensors and a processing unit, for example, to analyze data measured by the sensors. The sensors are electrically connected to the processing unit via the conductive threads embedded between the fabric layers of the garment. At least one hole on either side of the garment exposes a conductive thread. Holes in the garment also allow sensors and mounts to be placed on opposing sides of the garment. The sensors of the garment can be positioned such that particular data can be measured representative of a user wearing the garment during exercise. Examples of such data include a heart rate, a breathing rate, muscle activation data, electromyography or EMG data, exercise timing data, and the like.

The garment can be manufactured by bonding an adhesive to a first layer of fabric and a second layer of fabric. Holes are cut into each layer of fabric to accommodate the integration of sensors and a processing unit mount. Conductive thread embroidered onto a support layer is bonded to the adhesive of the second layer of fabric. The support layer is removed such that the conductive thread remains bonded to the adhesive. The first and second layers of fabric are bonded together such that the conductive thread is coupled between the two layers of adhesive. A back plate is added to the layers of fabric around at least one hole to provide structural support to maintain the position of the mount. The conductive thread is exposed within each hole, and the mount and sensors can be coupled within the holes such that an electrical connection is established between the mount and at least one sensor via the conductive thread.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Garment

Figure 1A:
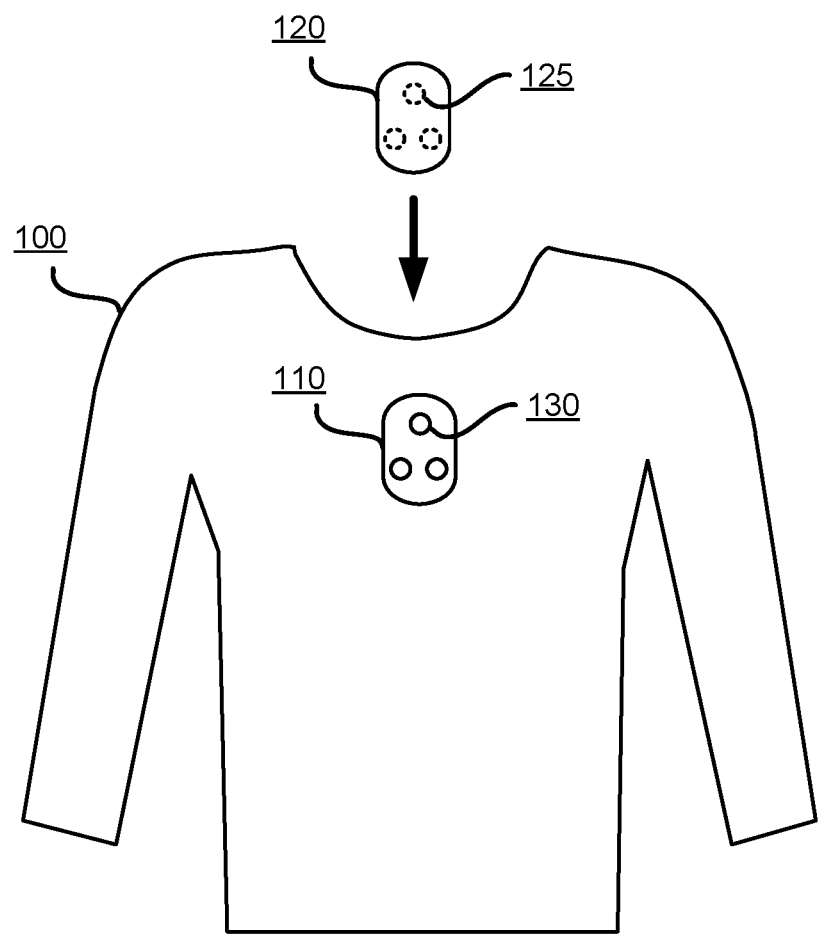
FIG. 1A shows an outside view of a garment according to one embodiment.

FIG. 1A shows an outside view of a garment 100 according to one embodiment. The garment 100 is coupled to a mount 110 for attaching a processing unit 120 to the garment 100. The processing unit 120 is also referred to herein as the "core." The processing unit 120 includes a first set of mount terminals 125, i.e., positioned on the bottom side of the processing unit 120, that are electrically conductive and are configured to receive signals for processing by the processing unit 120. Similarly, the mount 110 includes a second set of mount terminals 130, i.e., exposed on an outside surface of the garment 100 that are also electrically conductive, and are configured to output signals from sensors within the garment 100 to the processing unit 120. In some embodiments, the position and arrangement of the first set of mount terminals 125 corresponds to the position and arrangement of the second set of mount terminals 130 such that, for example, each terminal in the first set of mount terminals 125 makes physical contact with an associated terminal in the second set of mount terminals 130 when the processing unit 120 is coupled to the mount 110. FIG. 1A shows three mount terminals in each set positioned in a triangle configuration. In other embodiments, the sets of mount terminals include any number, position, or arrangement of mount terminals. The processing unit 120 receives electrical signals from the sensors in the garment 100 via both sets of mount terminals, for example, for processing, storage, and/or transmission to a mobile device or computing device.

The garment 100 is manufactured using multiple layers including at least a bottom layer of fabric, a layer of conductive thread (or other conductive materials or leads), and a top layer of fabric, i.e., the layer of fabric shown in FIG. 1A, coupled together using one or more layers of adhesive. Generally, each layer of fabric is less than 1 millimeter thick, e.g., approximately 0.5 millimeters thick, and can include any type of fabric, including but not limited to cotton, cotton hybrids, polyester, polypropylene, nylon, spandex/LYCRA®, or any blend or combination thereof. The manufacturing process is described in greater detail below. It should be noted that while the garment 100 shown in FIG. 1A is a long sleeve shirt, the principles described herein apply equally to any garment, including but not limited to a short sleeved shirt, a tank top, pants, shorts, or any other suitable garment.

Figure 1B:
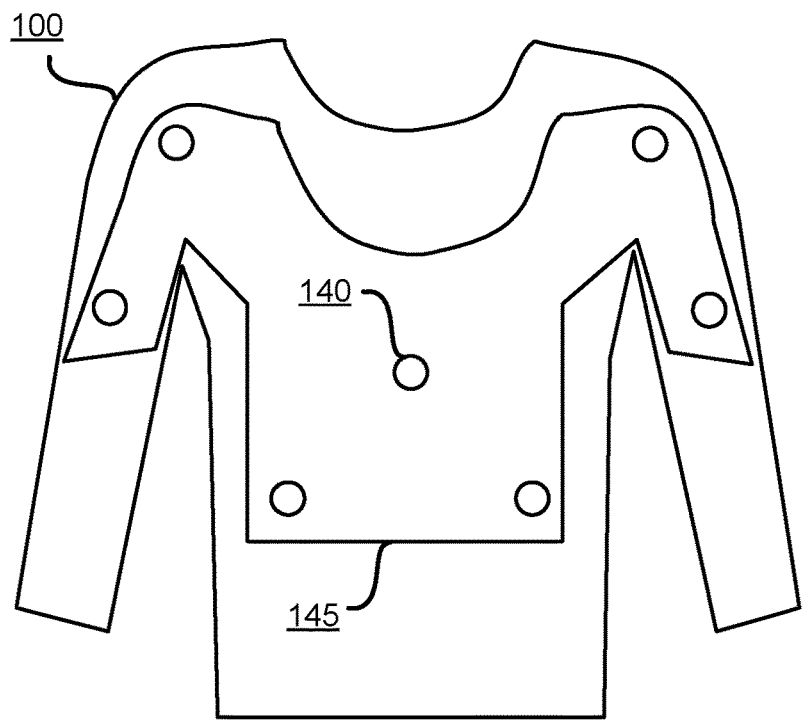
FIG. 1B shows an inside view of the garment with a bottom layer of fabric according to one embodiment.

FIG. 1B shows an inside view of the garment 100 with a bottom layer of fabric 145 according to one embodiment. In particular, FIG. 1B illustrates the bottom layer of fabric 145 (also referred to as an inner or inside layer of fabric) of the garment 100 coupled to the top layer of fabric shown in FIG. 1A. The garment 100 includes sensor terminals 140 exposed by holes in the bottom layer of fabric 145. In particular, the sensor terminals 140 are patches that overlap holes in the bottom layer of fabric 145, which allows a sensor (on an outer layer of fabric of the garment 100) to be electrically coupled to an internal layer of the garment 100, e.g., a layer of conductive thread. Sensors may be communicatively coupled to the sensor terminals 140 when physically coupled to the garment 100. Specifically, each sensor is positioned so that the sensor can make physical contact with the skin of a user wearing the garment 100 when the sensor is coupled to a corresponding sensor terminal 140. Sensors measure data from a user wearing the garment 100. For example, the sensors can be electrodes that measure electromyography (EMG) data of the user (electrical signals caused by muscle cells) or electrocardiograph (ECG) data of the user (electrical signals caused by depolarization of the user's heart muscle in particular). The sensors may also include other types of sensors such as temperature sensors, pressure sensors, humidity sensors, etc. The bottom layer of fabric 145 is not necessarily the same shape or size as the outer layer of fabric. Typically, the bottom layer of fabric 145 covers the sensor terminals 140 and is smaller than the outer layer of fabric. FIG. 1B shows seven sensor terminals 140 positioned in a symmetrical configuration on the bottom layer of fabric, though in other embodiments, the garment 100 can include any number or arrangement of sensor terminals 140.

Figure 1C:
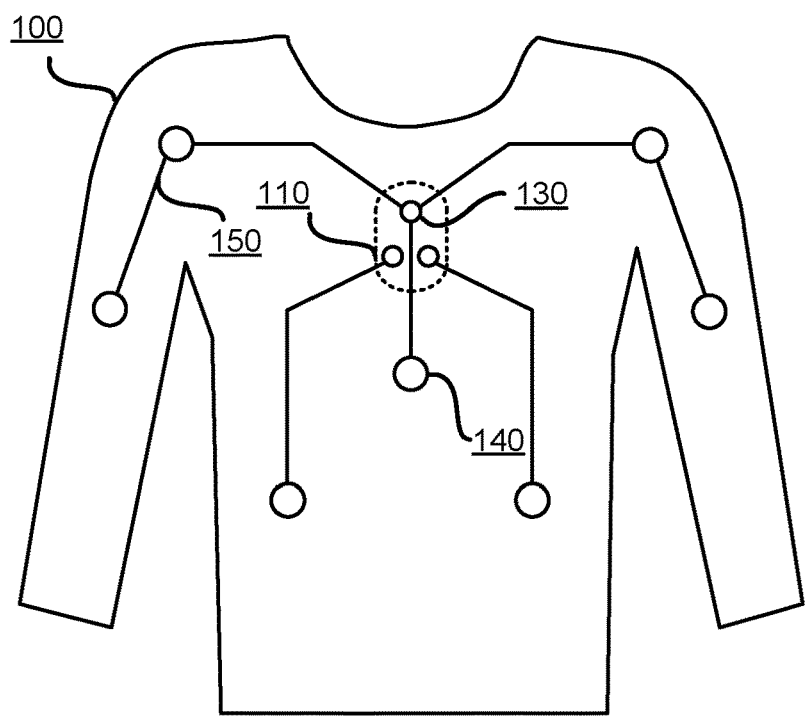
FIG. 1C shows an inside view of the garment with the bottom layer of fabric removed according to one embodiment.

FIG. 1C shows an inside view of the garment 100 with the bottom layer of fabric 145 (shown in FIG. 1B) removed according to one embodiment. The layer of conductive threads 150 is coupled between the top layer of fabric and the bottom layer of fabric. The conductive threads 150 can be a conductive resin (e.g., polymers, silicone, neoprene, thermoplastics, etc.), conductive metal (e.g., copper), or any other type of conductive material. The conductive resin is produced by combining conductive material with a resin, e.g., a non-conductive resin. The conductive threads 150 electrically couple the sensor terminals 140 to each other and/or to mount terminals 130. As discussed below, the conductive threads 150 can be embroidered onto a paper layer, which in turn can be coupled to an adhesive layer bonded to a fabric layer. In such embodiments, the paper portion of the paper layer can be removed, leaving the embroidered conductive threads coupled to the adhesive layer. Although the conductive threads 150 illustrated in FIG. 1C are straight lines, it should be noted that in other embodiments, the conductive threads can have curved patterns, zigzag patterns, and the like. Further, although some of the conductive threads 150 of FIG. 1C communicatively couple multiple sensor terminals 140 to a single mount terminal 130, it should be noted that in other embodiments, each sensor terminal 140 is communicatively coupled to a different mount terminal 130 by the conductive threads 150. In some embodiments, the conductive threads 150 do not overlap or cross within the garment 100. Generally, the conductive thread is less than 1 millimeter thick.

Figure 1D:
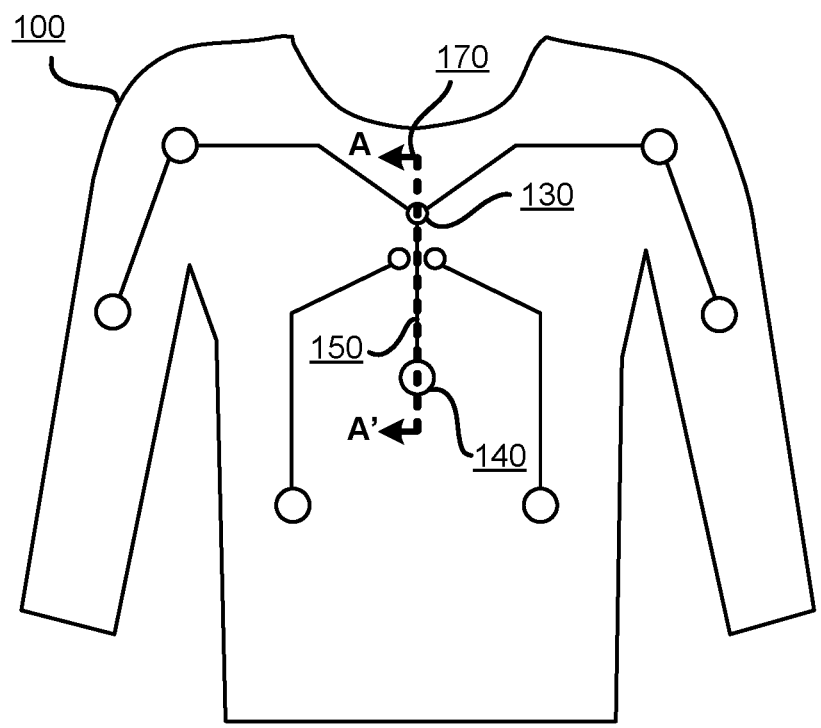
FIG. 1D shows another inside view of the garment with the bottom layer of fabric removed according to one embodiment.

FIG. 1D shows another inside view of the garment 100 with the bottom layer of fabric 145 (shown in FIG. 1B) removed according to one embodiment. In particular, FIG. 1D shows a cross section 170 (i.e., A-A') overlaid on the garment 100. The cross section 170 includes a mount terminal 130, sensor terminal 140, and segment of the conductive thread 150. The cross section 170 is further described with reference to FIGS. 2A-K below.

II. Cross Sections of Manufacturing Process

The garment 100 is manufactured using a process of steps to assemble multiple layers of the garment 100. FIGS. 2A-K illustrate this process with views of the cross section 170. The cross sectional views shown in FIGS. 2A-K are not necessarily to scale. In particular, the dimensions of various layers and components of the garment 100 have been altered for purposes of clarity.

II. A. Bottom Layer of Fabric

Figure 2A:
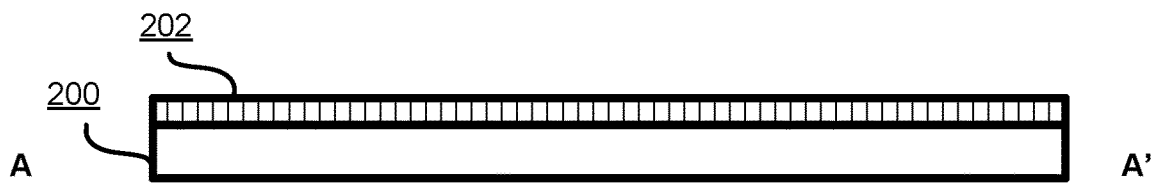
FIG. 2A shows a cross sectional view of a bottom layer of fabric bonded to an adhesive layer according to one embodiment.

FIG. 2A shows a cross sectional view of a bottom layer of fabric 200 bonded to an adhesive layer 202 according to one embodiment. As noted above, the fabric 200 can be composed of cotton, polyester, nylon, spandex, and the like. In some embodiments, the fabric 200 includes or is treated with anti-microbial material, moisture wicking material, and/or other chemical treatments. The adhesive 202 can be a polyurethane based adhesive, cyanoacrylate based adhesive, epoxy glue, or any other type of adhesive suitable for bonding fabric materials. The adhesive 202 is bonded to the top surface of the fabric 200. It should be noted that while the adhesive 202 is shown in the embodiment of FIG. 2A to cover the entirety of the surface of the fabric 200, in other embodiments, the adhesive 202 is applied only to portions of the fabric 200.

Figure 2B:
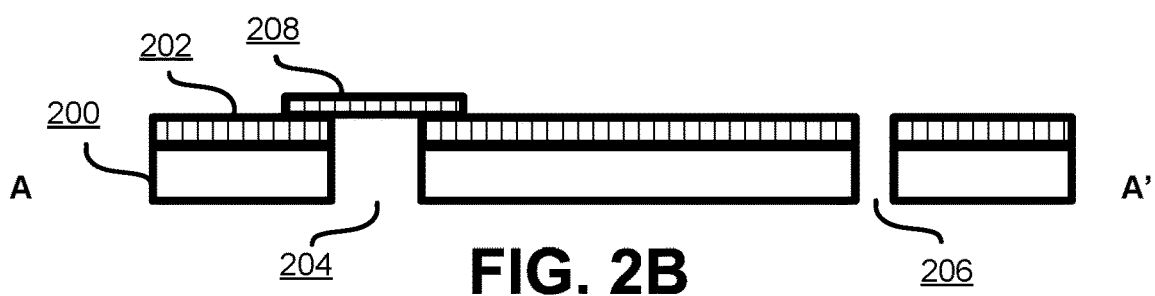
FIG. 2B shows a cross sectional view of the bottom layer of fabric with holes according to one embodiment.

FIG. 2B shows a cross sectional view of the bottom layer of fabric 200 with holes according to one embodiment. Specifically, the fabric 200 includes a mount hole 204 (to accommodate a back plate to support a mount for a processing unit 120, as described below) and a sensor hole 206 (to accommodate a sensor to make contact with a user). In some embodiments, the fabric 200 does not include a mount hole 204, and the back plate can be attached to the fabric 200 without using a mount hole 204. It should be emphasized that while the cross section illustrated in FIG. 2B includes only one sensor hole, in practice, the bottom layer of fabric of a garment 100 will include a multiple sensor holes, for instance 10 or more. In some embodiments, a pane 208 of adhesive, i.e., substantially the same material as the adhesive 202, is bonded over the mount hole 204, though in other embodiments, a pane of fabric or any other suitable material can be bonded over the mount hole 204.

Figure 2C:
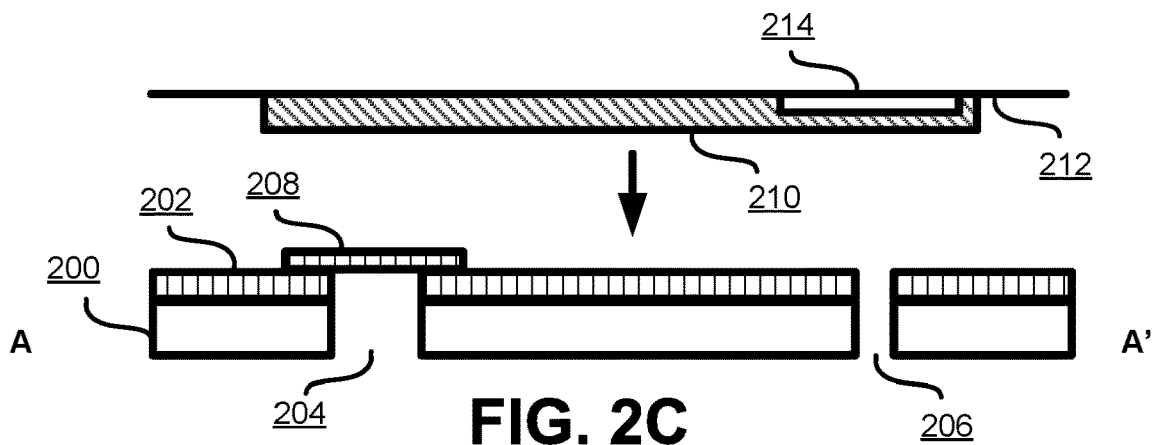
FIG. 2C shows a cross sectional view of the bottom layer of fabric and a paper layer embroidered with a conductive thread according to one embodiment.

FIG. 2C shows a cross sectional view of the bottom layer of fabric 200 and a paper layer 212 embroidered with conductive thread 210 according to one embodiment. The conductive thread 210 is embroidered onto a paper layer 212. Although reference is made herein to a paper layer 212, in other embodiments, the conductive thread 210 can be embroidered onto a support layer that is a wax paper layer, a plastic layer, a rubber layer, and the like according to the principles described herein. In some embodiments, the conductive thread 210 is not necessarily embroidered onto the support layer. For example, conductive material can be deposited onto the support layer using chemical vapor deposition, physical deposition, thermal treatment, spin-on film, sputtering, or any other suitable deposition method. The paper layer 212 includes a sensor support 214 coupled between the conductive thread 210 and the paper layer 212 such that the sensor support 214 aligns with the sensor hole 206 when the paper layer 212 is bonded to the fabric 200. The sensor support 214 can be an adhesive, a fabric, plastic, rubber, and the like or combinations thereof. The paper layer 212 is bonded to the fabric 200 such that the conductive thread 210 is coupled between the adhesive 202 and the paper layer 212, and such that the sensor support 214 is aligned with the sensor hole 206. In some embodiments, the paper layer 212 is not necessarily composed using a paper type material. For example, the paper layer 212 is made using plastic or a synthetic material and may be referred to as a support layer.

Figure 2D:
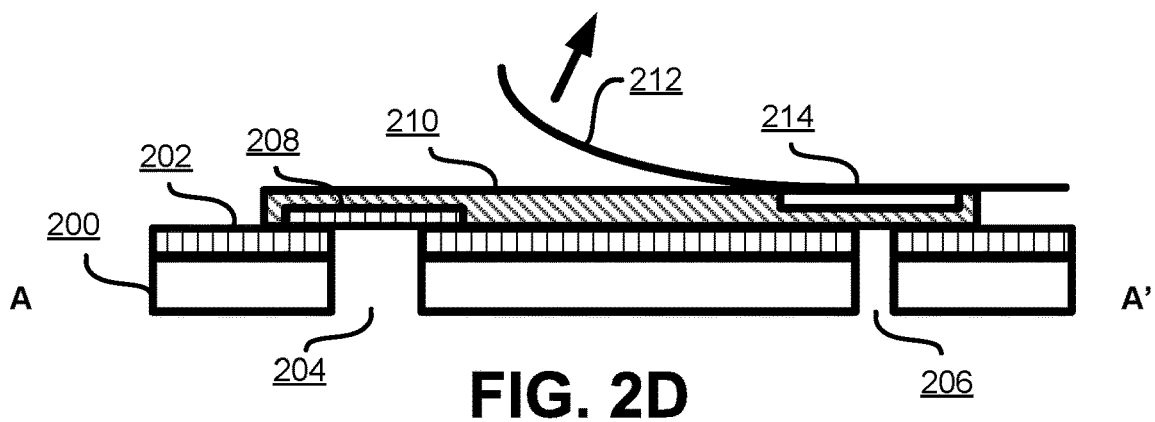
FIG. 2D shows a cross sectional view of the bottom layer of fabric coupled to the conductive thread according to one embodiment.

FIG. 2D shows a cross sectional view of the bottom layer of fabric 200 coupled to the conductive thread 210 according to one embodiment. The paper layer 212 is removed from the fabric 200 such that the conductive thread 210 remains coupled to the fabric 200. In some embodiments, the paper layer 212 can be peeled away from the fabric 200, while in other embodiments, a chemical treatment or other substance can be applied to the paper layer 212, causing the paper layer 212 to separate from the conductive thread 210.

II. B. Top Layer of Fabric

Figure 2E:
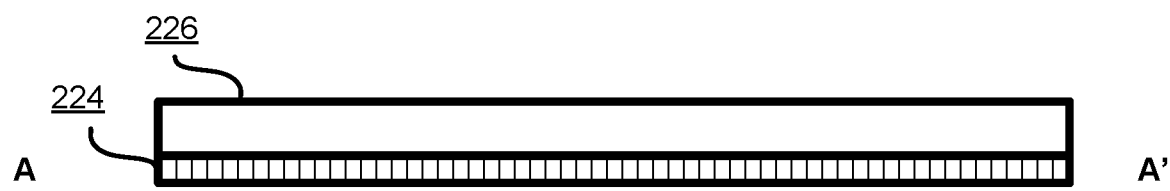
FIG. 2E shows a cross sectional view of a top layer of fabric bonded to an adhesive layer according to one embodiment.

FIG. 2E shows a cross sectional view of a top layer of fabric 226 bonded to an adhesive layer 224 according to one embodiment. The top layer of fabric 226 and adhesive layer 224 can be made of the same materials as the bottom layer of fabric 200 and the adhesive layer 202 described in FIG. 2A, respectively, or can be made of different materials. The adhesive layer 224 is bonded to the bottom surface of the fabric 226. It should be noted that while the adhesive layer 224 is shown in the embodiment of FIG. 2E to cover the entirety of the surface of the fabric 226, in other embodiments, the adhesive layer 224 is applied only to portions of the fabric 226.

Figure 2F:
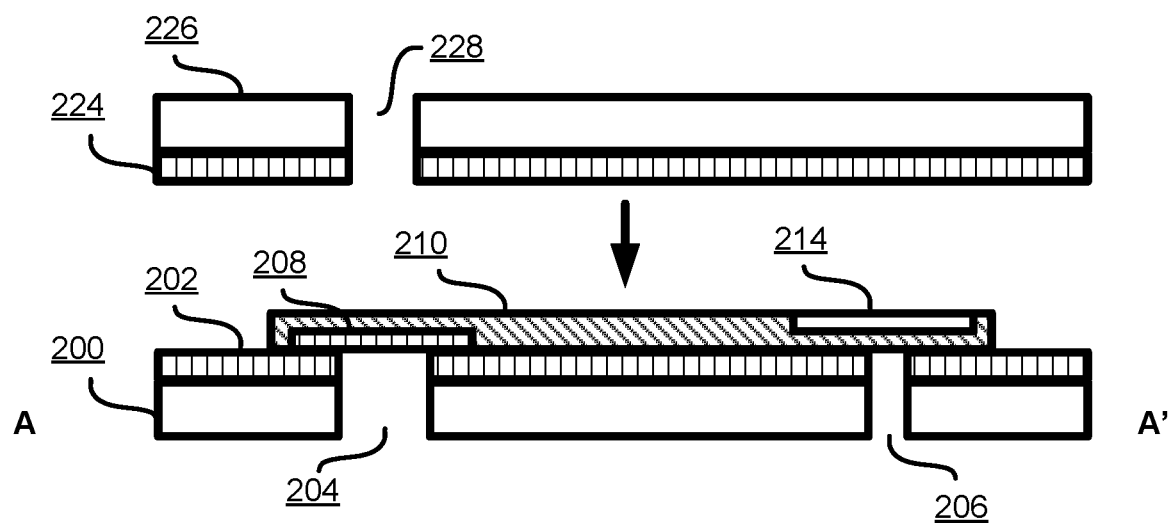
FIG. 2F shows a cross sectional view of the top layer of fabric with a mount terminal hole according to one embodiment.

FIG. 2F shows a cross sectional view of the top layer of fabric 226 with a mount terminal hole 228 according to one embodiment. The mount terminal hole 228 is cut out to accommodate a mount terminal, for example, the mount terminal 130 shown in FIG. 1C. It should be emphasized that while the cross section illustrated in FIG. 2F includes only one mount terminal hole 228, in practice, the top layer of fabric of a garment 100 can include multiple mount terminal holes, for instance, one for each mount terminal of a mount 110 attached to the garment 100.

In some embodiments, the mount terminal hole 228 is not cut out, but formed using other techniques. For example, the top layer of fabric 226 includes multiple segments. At least two of the segments have indentations. Thus, coupling the two segments together may form the mount terminal hole 228. For instance, each indentation is a semicircle such that coupling the two segments together—aligning the two indentations—forms a circular shaped hole. Other holes of the garment 100 (e.g., mount hole 204 and sensor hole 206) can be formed similarly using various techniques other than cutting.

Figure 2G:
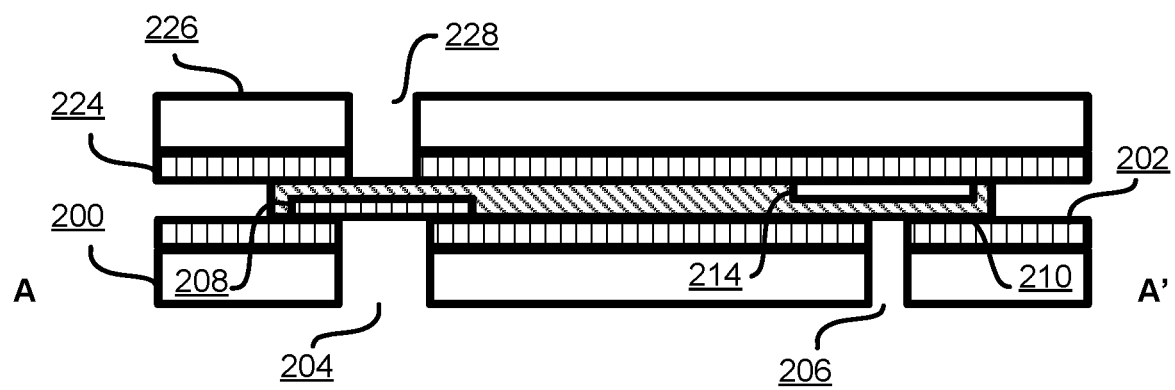
FIG. 2G shows a cross sectional view of the bottom layer of fabric coupled to the top layer of fabric according to one embodiment.

FIG. 2G shows a cross sectional view of the bottom layer of fabric 200 coupled to the top layer of fabric 226 according to one embodiment. The bottom layer of fabric 200 is coupled to the top layer of fabric 226 via the adhesive layers 202 and 224 such that the conductive thread 210 is coupled between the adhesives layers, and such that the mount terminal hole 228 aligns with the mount hole 204. In some embodiments, the adhesive layers 202 and 224 each include an internal waterproof barrier layer. The internal waterproof barrier layers each contact the conductive thread 210. Thus, the conductive thread 210 is protected from moisture or other contaminants by the internal waterproof barrier layers. It should be noted that although the embodiment of FIG. 2G includes gaps between portions of the adhesive layers 202 and 224 not immediately adjacent to the conductive thread 210, in practice, the conductive thread 210 is very thin (e.g., less than 1 millimeter thick), allowing the adhesive layers 202 and 224 to compress together around the conductive thread 210.

As illustrated in the embodiment of FIG. 2G, the conductive thread 210 is exposed within the mount terminal hole 228. A mount terminal of a mount 110 can be inserted into the mount terminal hole 228 such that the mount terminal abuts the exposed portion of the conductive thread 210. Thus, the mount terminal can be electrically coupled to the conductive thread 210 and, in turn, to a sensor electrically coupled to the conductive thread 210. Signals from such a sensor can be transmitted to the mount terminal (and to a processing unit or core electrically coupled to the mount 110) via the conductive thread 210. Similarly, the conductive thread 210 is also exposed within the sensor hole 206, thereby enabling a sensor inserted into the sensor hole 206 such that the sensor abuts the portion of the exposed conductive thread 210 to be electrically coupled to the conductive thread 210 and, in turn, to a mount terminal and processing unit also electrically coupled to the conductive thread 210.

II. C. Mount and Sensor

Figure 2H:
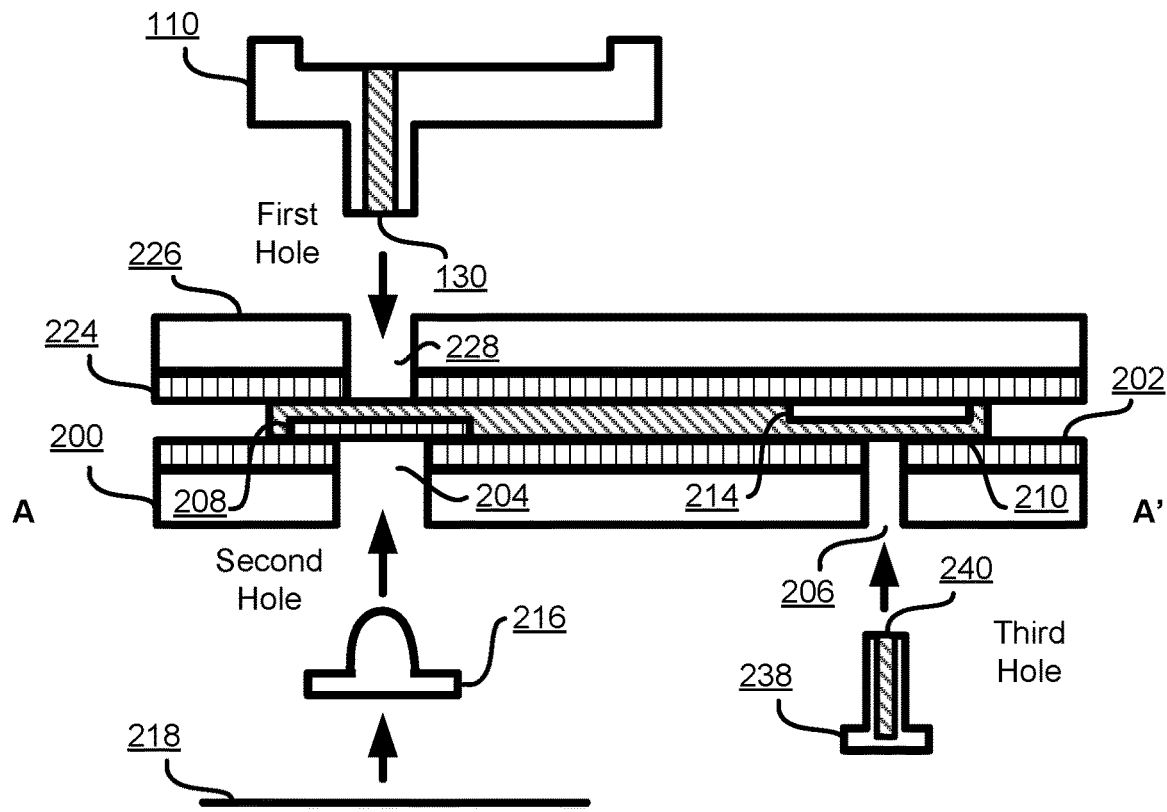
FIG. 2H shows a cross sectional view of the coupled layers of fabric, a mount, and a sensor according to one embodiment.

FIG. 2H shows a cross sectional view of the coupled layers of fabric 200 and 226, a mount 110, and a sensor 238 according to one embodiment. The mount 110 includes a mount terminal 130, for example, one of the mount terminals in the first set of mount terminals 130 shown in FIG. 1A. The sensor 238 (previously described with reference to FIG. 1B) includes an electrically conductive terminal 240. The mount 110 is coupled to the coupled layers of fabric 200 and 226 by aligning the mount terminal 130 with and overlapping the mount terminal 130 into the mount terminal hole 228 (also referred to as the second hole). The mount terminal 130 can form a waterproof seal over the second hole. The sensor 238 is coupled to the coupled layers of fabric 200 and 226 by aligning the terminal 240 with and overlapping the sensor 238 into the sensor hole 206 (also referred to as the third hole). The sensor 238 can form a waterproof seal over the third hole. In one embodiment, the sensor 238 is coupled to the garment 100 using a liquid conductive silicone to form an electrical connection to the conductive thread 210. The liquid conductive silicone cures to form a solid seal.

FIG. 2H also shows a back plate 216 and a protective layer 218. The back plate 216 is a rigid or semi-rigid material, such as plastic. The protective layer 218 prevents the skin of a user wearing the garment 100 from directly physically contacting the back plate 216, beneficially increasing the comfort of a user wearing the garment 100. The protective layer 218 can also form a waterproof seal over holes or access points in the bottom layer of fabric 200. The protective layer 218 can be a fabric, plastic, rubber, and the like.

The back plate 216 can be coupled to the bottom layer of fabric 200 by applying an adhesive on a top surface of the protective layer 218 around the back plate 216 and compressing the protective layer 218 into the bottom layer of fabric 200. The back plate 216 can also be coupled to the bottom layer of fabric using any other suitable method, including but not limited to sewing the fabric 200 and the protective layer 218 together. As will be described below, the back plate 216 provides structural support to the mount 110 when the mount 110 is coupled to the garment 100. Accordingly, the back plate 216 is aligned with and overlaps with the mount hole 204 when the back plate 216 is coupled to the layer of fabric 200. In some embodiments, the top of the back plate 216 physically abuts the pane 208 before the mount 110 is coupled to the garment 110, while in other embodiments, the mount 110 compresses the conductive thread 210 and the pane 208 into the top of the back plate 216.

It should be noted that each of the holes 204, 206, and 228, as well as portions of the mount 110, sensor 238, and back plate 216 that overlap with the holes, have been enlarged as illustrated in FIG. 2H for purposes of clarity. In practice, each of the holes 204, 206, and 228 are thin because the coupled layers of fabric 200 are each typically less than 1 millimeter in thickness.

Figure 2I:
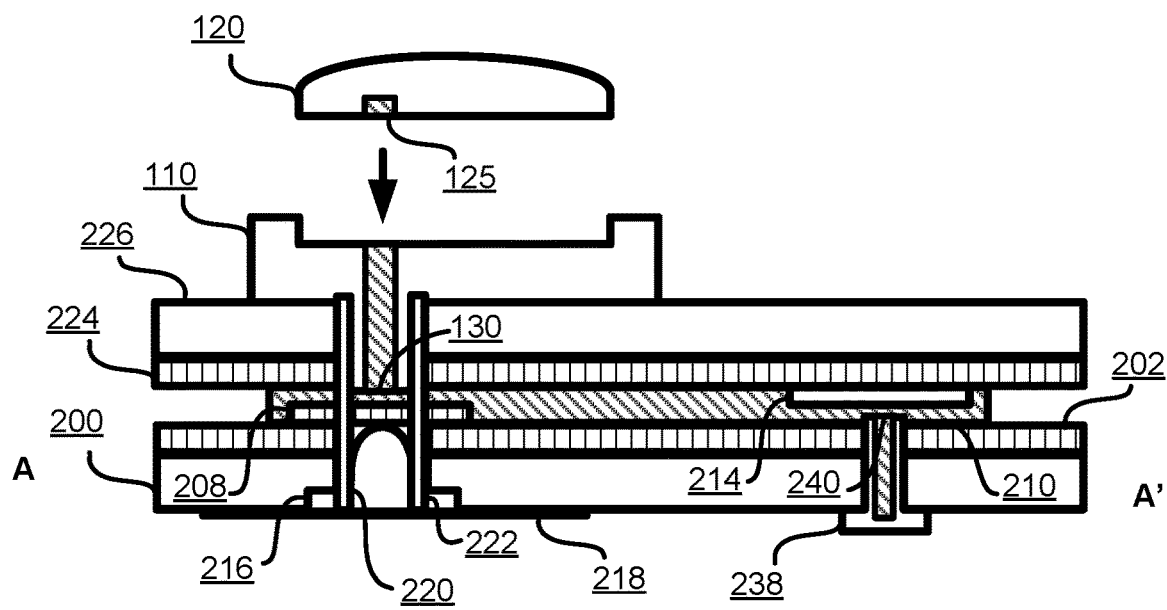
FIG. 2I shows a cross sectional view of the coupled layers of fabric coupled to the mount and the sensor according to one embodiment.

FIG. 2I shows a cross sectional view of the coupled layers of fabric 200 and 226 coupled to the mount 110 and the sensor 238 according to one embodiment. The back plate 216 and protective layer 218 are also coupled to the bottom layer of fabric 200. The mount terminal 130 physically abuts and/or compresses the conductive thread 210. Further, the terminal 240 of the sensor 238 also physically abuts and/or compresses the conductive thread 210. Thus, the mount terminal 130 is electrically coupled to the terminal 240 via the conductive thread 210, thereby enabling the mount 110 to receive signals from the sensor 238 (and in some embodiments, transmit signals to the sensor 238). The mount 110 is coupled to the back plate 216 via screws 220 and 222 (or bolts and the like) through the back plate 216 and the mount 110. In some embodiments, the mount 110 is coupled to the fabric layer 226 via an adhesive.

When the mount 110 abuts and/or compresses the conductive thread 210, the back plate 216 asserts a reciprocal compressive force on the conductive thread 210, thereby securing the mount 110 against the back plate 216. In other words, the conductive thread 210 is compressibly secured between the mount 110 and the back plate 216, beneficially securing the electrical coupling between the mount terminal 130 and the conductive thread 210. In some embodiments, the mount 110, the sensor 238, and the layers of adhesive 202 and 224 provide a waterproof seal around the openings, protecting the conductive thread 210.

The processing unit 120 includes at least one mount terminal 125, for example, one of the mount terminals 125 shown in FIG. 1A. The processing unit 120 can be coupled to the mount 110 such that the mount terminal 125 is aligned with the mount terminal 130, and such that the processing unit 120 can transmit signals to and from the sensor 238 via the mount terminal 130, the conductive thread 210, and the terminal 240. Though only one electrical connection between the processing unit 120 and a sensor 238 is shown in a garment in FIG. 2I, typically, a garment 100 includes multiple electrical connections between mount terminals and sensors.

Figure 2J:
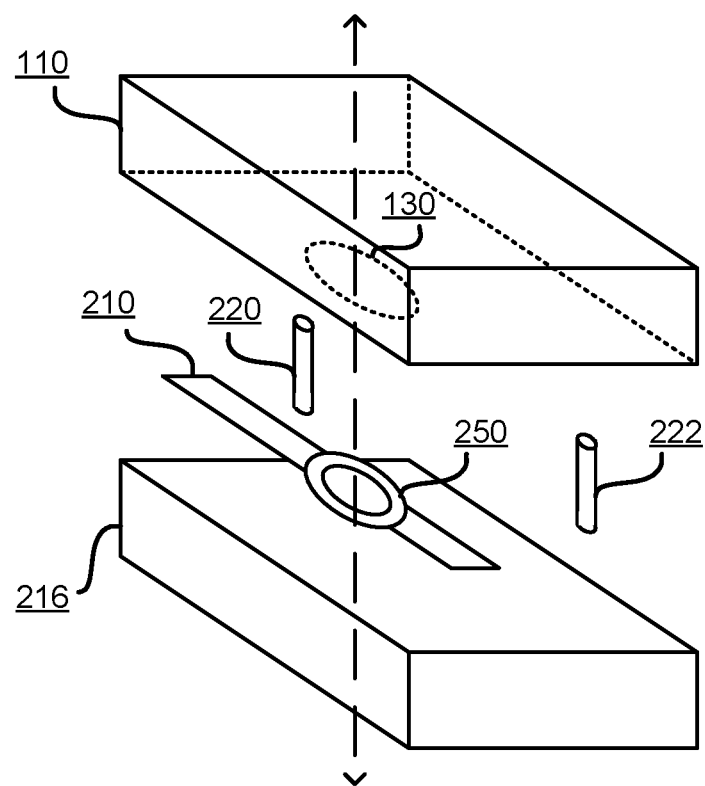
FIG. 2J shows an isometric view of a grommet of the garment according to one embodiment.

FIG. 2J shows an isometric view of a grommet 250 of the garment 100 according to one embodiment. For purposes of clarity, only select components of the garment 100 shown in FIG. 2I are shown in FIG. 2J. In addition to the components shown in FIG. 2I, the conductive thread 210 is coupled to a grommet 250. The grommet 250 helps form an electrical connection between the conductive thread 210 and the mount 110 or the sensor 238, e.g., by providing mechanical support. In particular, the screws 220 and 222 that couple the mount 110 to the back plate 216 compress the grommet 250 in between, which keeps the grommet 250 secured in place. Thus, the grommet 250 stays aligned to the mount terminal 130 (or a sensor terminal 140). Though only one grommet is shown in FIG. 2J, it should be noted that the garment 100 typically includes multiple grommets, e.g., a grommet for each connection to the mount 110 or sensors 238.

III. Method of Manufacture

Figure 3:
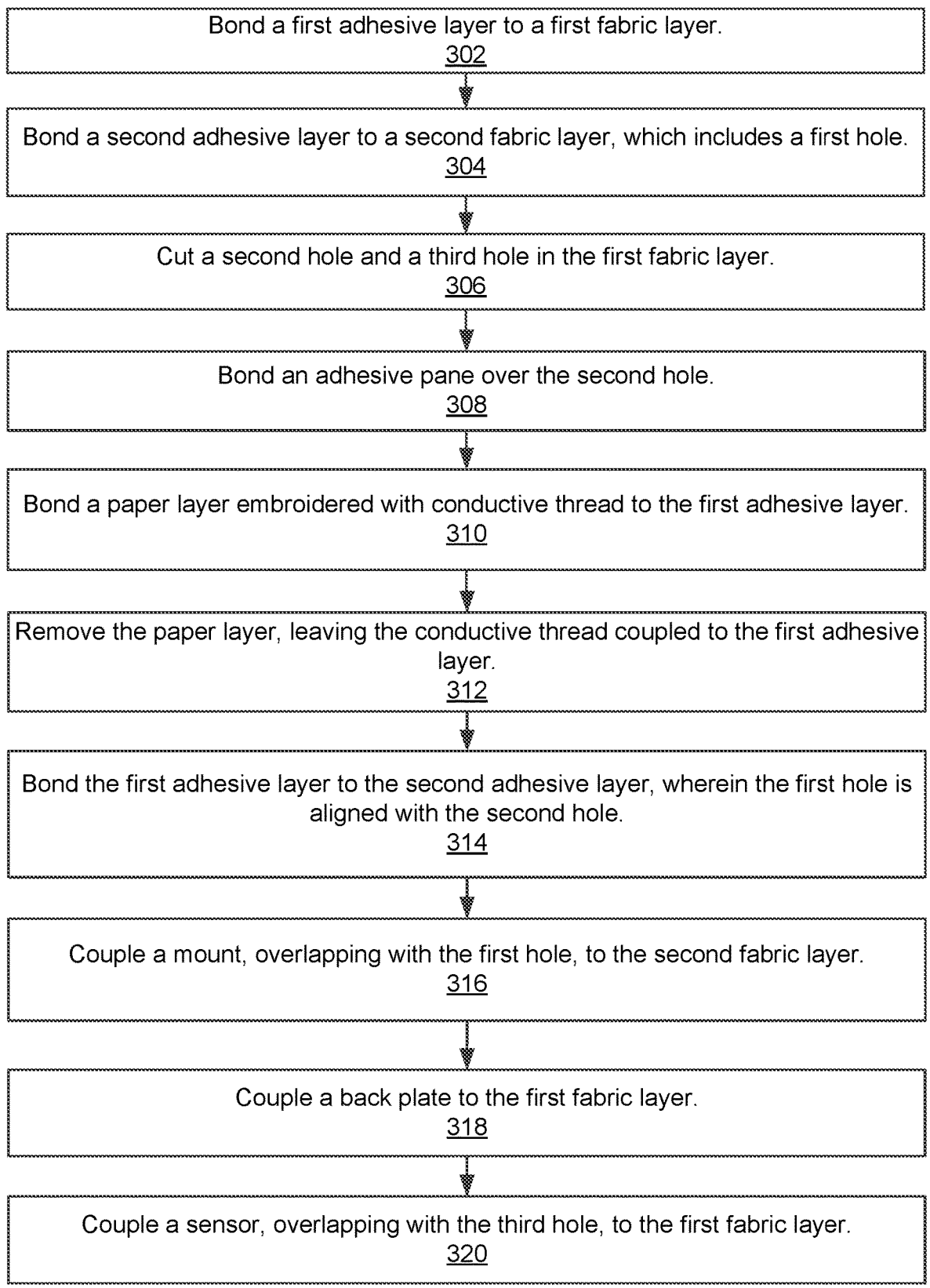
FIG. 3 is a flow chart illustrating a process for manufacturing a garment according to one embodiment.

FIG. 3 is a flow chart illustrating a process 300 for manufacturing a garment 100 according to one embodiment. In some embodiments, the process 300 may include different or additional steps than those described in conjunction with FIG. 3, and in some embodiments, the process 300 includes steps in different orders than the order described in conjunction with FIG. 3.

The process 300 manufactures a garment 100 layer by layer using varying materials and components. A first adhesive layer (for instance, the adhesive layer 202 as shown in FIG. 2A) is bonded 302 to a first fabric layer (for instance, the fabric layer 200). A second adhesive layer (such as the adhesive layer 224 shown in FIG. 2E) is bonded 304 to a second fabric layer (such as the fabric layer 226), which includes a first hole. A second hole and a third hole (for instance, the mount hole 204 and sensor hole 206 shown in FIG. 2B, respectively) are cut 306 into the bonded first adhesive layer and the first fabric layer.

An adhesive pane (for instance, the pane 208 shown in FIG. 2B) is bonded 308 over the second hole and is coupled to the first adhesive layer. A paper layer embroidered with conductive thread (for instance, the paper layer 214 as shown in FIG. 2C) is bonded 310 to the first adhesive layer. The paper layer is removed 312 from the first adhesive layer such that the conductive thread remains coupled to the first adhesive layer (for instance, as shown in FIG. 2D).

The first adhesive layer is bonded 314 to the second adhesive layer such that the first hole is aligned with the second hole (for instance, the mount hole 204 is aligned with the mount terminal hole 228, as shown in FIG. 2G). In addition, the conductive thread is coupled between the first adhesive layer and the second adhesive layer, and is exposed within the first hole and the third hole. A mount is coupled 316 to the second fabric layer such that the mount overlaps with the first hole and makes electrical contact with the conductive thread exposed at the first hole (for instance, as shown in FIG. 2H). A back plate (for instance, the back plate 216 shown in FIG. 2I) is coupled 318 to the first fabric layer such that the back plate overlaps with the second hole. A sensor is coupled 320 to the first fabric layer such that the sensor overlaps with the third hole and makes electrical contact with the conductive thread exposed at the third hole (for instance, as shown in FIG. 2H).

IV. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A garment manufactured by a process comprising the steps of:
   bonding a first adhesive layer to a first fabric layer;
   bonding a second adhesive layer to a second fabric layer including a first hole;
   cutting a second hole and a third hole into the first adhesive layer and the first fabric layer;
   bonding an adhesive pane over the second hole, the adhesive pane coupled to the first adhesive layer;
   bonding a support layer embroidered with conductive thread to the first adhesive layer;
   removing the support layer from the first adhesive layer such that the conductive thread remains coupled to the first adhesive layer;
   bonding the first adhesive layer to the second adhesive layer such that the first hole is aligned with the second hole, such that the conductive thread is coupled between the first adhesive layer and the second adhesive layer, and such that the conductive thread is exposed at the first hole and the third hole;
   coupling a mount to the second fabric layer such that the mount overlaps with the first hole and makes electrical contact with the conductive thread exposed at the first hole;
   coupling a back plate to the first fabric layer such that the back plate overlaps with the second hole, wherein the back plate physically abuts the adhesive pane and compresses the pane of adhesive and the conductive thread coupled to the pane of adhesive into the mount; and
   coupling a sensor to the first fabric layer such that the sensor overlaps with the third hole and makes electrical contact with the conductive thread exposed at the third hole.

2. The garment of claim 1, wherein the second fabric layer includes a plurality of segments, at least two of the segments each including an indentation, and wherein the first hole is formed by the indentations of the at least two of the plurality of segments.

3. The garment of claim 1, wherein a grommet is coupled to the conductive thread exposed within the first hole.

4. The garment of claim 1, wherein the first adhesive layer and the second adhesive layer provide a waterproof seal around the conductive thread.

5. The garment of claim 1, wherein the sensor comprises an electrode configured to record electromyography (EMG) or electrocardiograph (ECG) data and to provide the data to a processing unit electrically coupled to the mount via the conductive thread.

6. The garment of claim 1, wherein conductive thread is a conductive resin.

7. The garment of claim 1, wherein the conductive thread is less than 1 millimeter thick, the first layer of fabric is less than 1 millimeter thick, and the second layer of fabric is less than 1 millimeter thick.

8. The garment of claim 1, wherein the first fabric layer is larger in size than the second fabric layer.

9. A method comprising:
   bonding a first adhesive layer to a first fabric layer;
   bonding a second adhesive layer to a second fabric layer including a first hole;
   cutting a second hole and a third hole into the first adhesive layer and the first fabric layer;
   bonding an adhesive pane over the second hole, the adhesive pane coupled to the first adhesive layer;
   bonding a support layer embroidered with conductive thread to the first adhesive layer;
   removing the support layer from the first adhesive layer such that the conductive thread remains coupled to the first adhesive layer;
   bonding the first adhesive layer to the second adhesive layer such that the first hole is aligned with the second hole, such that the conductive thread is coupled between the first adhesive layer and the second adhesive layer, and such that the conductive thread is exposed at the first hole and the third hole;

coupling a mount to the second fabric layer such that the mount overlaps with the first hole and makes electrical contact with the conductive thread exposed at the first hole;

coupling a back plate to the first fabric layer such that the back plate overlaps with the second hole, wherein the back plate physically abuts the adhesive pane and compresses the pane of adhesive and the conductive thread coupled to the pane of adhesive into the mount; and coupling a sensor to the first fabric layer such that the sensor overlaps with the third hole and makes electrical contact with the conductive thread exposed at the third hole.

10. The method of claim 9, wherein the second fabric layer includes a plurality of segments, at least two of the segments each including an indentation, and wherein the first hole is formed by the indentations of the at least two of the plurality of segments.

11. The method of claim 9, wherein a grommet is coupled to the conductive thread exposed within the first hole.

12. The method of claim 9, wherein the first adhesive layer and the second adhesive layer provide a waterproof seal around the conductive thread.

13. The method of claim 9, wherein the sensor comprises an electrode configured to record electromyography (EMG) or electrocardiograph (ECG) data and to provide the data to a processing unit electrically coupled to the mount via the conductive thread.

14. The method of claim 9, wherein conductive thread is a conductive resin.

15. The method of claim 9, wherein the conductive thread is less than 1 millimeter thick, the first layer of fabric is less than 1 millimeter thick, and the second layer of fabric is less than 1 millimeter thick.

16. The method of claim 9, wherein the first fabric layer is larger in size than the second fabric layer.

17. A garment comprising:
a first garment layer including a first hole;
a second garment layer including a second hole, wherein the first hole and the second hole are aligned and located on opposite sides of the garment;
a conductive thread coupled, using a first adhesive layer coupled to the first garment layer and a second adhesive layer coupled to the second garment layer, such that the conductive thread is positioned between the first and the second adhesive layers and exposed within the first hole and the second hole;
a mount coupled to the second garment layer such that the mount overlaps with the second hole and makes electrical contact with the conductive thread exposed at the second hole;
a back plate coupled to the first garment layer and overlapping with the second hole, wherein the back plate physically abuts the second adhesive layer and compresses the second adhesive layer and the conductive thread coupled to the second adhesive layer into the mount; and
a sensor coupled to the first fabric layer and electrically coupled to the conductive thread.

18. The garment of claim 17, wherein the first and the second adhesive layers each include an internal waterproof barrier layer.

19. A method comprising:
cutting a first hole and a second hole into a first garment layer;
cutting a third hole into a second garment layer;
bonding an adhesive pane over the first hole, the adhesive pane coupled to the first garment layer;
bonding a second adhesive layer to the second garment layer;
bonding a conductive layer to the first garment layer and adhesive pane, the conductive layer comprising a conductive lead;
coupling a back plate to the first garment layer such that the back plate overlaps with the second hole, wherein the back plate physically abuts the adhesive pane and compresses the adhesive pane and the conductive lead coupled to the adhesive pane into a mount;
bonding the first garment layer to the second adhesive layer bonded to the second garment layer such that the first hole is aligned with the third hole, such that the conductive lead is coupled between the first garment layer and the second garment layer, and such that the conductive lead is exposed at both the second hole and the third hole; and
coupling a sensor to the first fabric layer and to the conductive lead by way of the third hole.

* * * * *